United States Patent [19]

Scheffler et al.

[11] Patent Number: 5,944,969
[45] Date of Patent: Aug. 31, 1999

[54] ELECTROCHEMICAL SENSOR WITH A NON-AQUEOUS ELECTROLYTE SYSTEM

[75] Inventors: Towner B. Scheffler, Butler; Joseph D. Jolson, Pittsburgh, both of Pa.

[73] Assignee: Mine Safety Appliances Company, Pittsburgh, Pa.

[21] Appl. No.: 08/896,630

[22] Filed: Jul. 18, 1997

Related U.S. Application Data

[63] Continuation of application No. 08/617,504, Mar. 15, 1996, abandoned.

[51] Int. Cl.$^6$ .................................................. G01N 27/404
[52] U.S. Cl. ........................ 204/415; 204/412; 204/432; 205/779.5; 205/780; 205/783; 205/786.5
[58] Field of Search ........................... 204/415; 205/782, 205/782.5, 783

[56] References Cited

U.S. PATENT DOCUMENTS

| | | |
|---|---|---|
| 4,169,779 | 10/1979 | Tataria et al. ........................... 204/415 |
| 4,479,865 | 10/1984 | Beder et al. ............................. 204/415 |
| 4,522,690 | 6/1985 | Venkatasetty ........................... 204/415 |
| 4,536,274 | 8/1985 | Papadakis et al. ..................... 204/415 |
| 4,604,182 | 8/1986 | Seago ...................................... 204/415 |
| 4,851,088 | 7/1989 | Chandrasekhar et al. ............. 204/415 |
| 5,120,585 | 6/1992 | Sutter et al. ........................... 428/34.2 |
| 5,554,414 | 9/1996 | Moya et al. ............................ 427/244 |

*Primary Examiner*—T. Tung
*Attorney, Agent, or Firm*—James G. Uber; Henry E. Bartony, Jr.

[57] ABSTRACT

Accordingly, the present invention provides an electrochemical sensor comprising at least two electrochemically active electrodes, a non-aqueous electrolyte system and a diffusion barrier membrane through which the analyte in its gas phase is mobile but through which the non-aqueous electrolyte system is substantially immobile. The diffusion barrier membrane thus allows an analyte in its gas phase to enter the sensor, while substantially preventing the non-aqueous electrolyte from exiting the sensor.

12 Claims, 3 Drawing Sheets

ELECTROCHEMICAL SENSOR WITH A NON-AQUEOUS ELECTROLYTE SYSTEM

This application is a continuation of application Ser. No. 08/617,504 filed on Mar. 15, 1996, now abandoned.

FIELD OF THE INVENTION

The present invention relates to electrochemical sensors, and, particularly to electrochemical sensors comprising a non-aqueous electrolyte system and a diffusion barrier through which the analyte is mobile in its gas phase but through which the electrolyte system is substantially immobile.

BACKGROUND OF THE INVENTION

Electrochemical sensors or cells are widely used to determine electrochemically active chemical species in liquid, gas and vapor phases. Such electrochemical sensors can be conveniently classified as galvanic when operated to produce electrical energy and electrolytic when operated at a constant potential via consumption of electrical energy from an external source. Many electrochemical sensors can be operated in either a galvanic or an electrolytic mode.

In an electrochemical sensor, the chemical species to be measured (the "analyte") typically diffuses from the test environment into the sensor housing through an analyte-porous or analyte-permeable membrane to a working electrode (sometimes called a sensing electrode) wherein the analyte chemically reacts. A complementary chemical reaction occurs at a second electrode in the sensor housing known as a counter electrode (or an auxiliary electrode). The electrochemical sensor produces an analytical signal via the generation of a current arising directly from the oxidation or reduction of the analyte gas at the working and counter electrodes.

In general, the electrodes of an electrochemical sensor provide a surface at which an oxidation or a reduction reaction occurs (that is, an electrochemically active surface) to provide a mechanism whereby the ionic conduction of an electrolyte solution in contact with the electrodes is coupled with the electron conduction of each electrode to provide a complete circuit for a current. By definition, the electrode at which an oxidation occurs is the anode, while the electrode at which the "complimentary" reduction occurs is the cathode.

To be useful as an electrochemical sensor, a working and counter electrode combination must be capable of producing an electrical signal that is (1) related to the concentration of the analyte and (2) sufficiently strong to provide a signal-to-noise ratio suitable to distinguish between concentration levels of the analyte over the entire range of interest. In other words, the current flow between the working electrode and the counter electrode must be measurably proportional to the concentration of the analyte over the concentration range of interest.

In addition to a working electrode and a counter electrode, an electrolytic electrochemical sensor often includes a third electrode, commonly referred to as a reference electrode. A reference electrode is used to maintain the working electrode at a known voltage or potential. The reference electrode should be physically and chemically stable in the electrolyte and carry the lowest possible current to maintain a constant potential.

As discussed above, the electrical connection between the working electrode and the counter electrode is maintained through an electrolyte. The primary functions of the electrolyte are: (1) to efficiently carry the ionic current; (2) to solubilize the analyte in its gas phase; (3) to support both the counter and the working electrode reactions; and (4) to form a stable reference potential with the reference electrode. The primary criteria for an electrolyte include the following: (1) electrochemical inertness; (2) ionic conductivity; (3) chemical inertness; (4) temperature stability; (5) low cost; (6) low toxicity; (7) low flammability; and (8) appropriate viscosity.

Electrochemical sensors typically use aqueous electrolytes and porous hydrophobic membranes as electrode supports and as gas diffusion barriers. In other words, such porous membranes perform two functions: (1) acting as a support for an electrochemically active material such as an electrocatalyst; and (2) acting as a diffusion barrier. The diffusion barrier allows diffusion of the analyte in its gas phase into the sensor to contact the electrocatalyst, while effectively retaining the aqueous electrolyte within the interior of the sensor.

The most commonly used aqueous electrolytes incorporate solutions of sulfuric acid, in part, because of their insensitivity to carbon dioxide ($CO_2$) which is commonly present in test environments. Moreover, sulfuric acid provides an aqueous electrolyte containing a nonvolatile solute. Unfortunately, the use of aqueous electrolytes is restricted by a number of factors, including the range of electrical potentials at which water decomposes and by the high vapor pressure of water. Aqueous electrolytes also have a high dielectric constant and, therefore, can generally dissolve more gas. However, such high gas dissolution rates create a number of measurement distortions.

Most electrochemical toxic sensors employing aqueous electrolyte solutions include porous polytetrafluoroethylene (PTFE) diffusion barrier membranes such as Gore-Tex® or Zitex®. These materials provide a generally effective means of fabricating a variety of useful sensors with generally acceptable output characteristics. For example, such sensors exhibit adequate sensitivity, long life (typically at least one year, and up to five years or more) and freedom from liquid leaks over the lifetime of the sensor. Current diffusion barriers made from materials such as Gore-Tex and Zitex generally operate best under conditions in which the pH of the electrolyte solution is less than 7.0. Such diffusion barriers often fail at a pH above 7.0 or if a solute, such as a charge carrier, is added to the electrolyte solution. It is believed that such failure (that is, bulk passage of electrolyte through the membrane) is associated with a reduction of surface tension.

Very little research has been performed with electrochemical systems comprising "non-aqueous" electrolytic solutions. This lack of research may stem, in part, from the unfeasibility of excluding water from such systems during use. Moreover, current diffusion barrier membranes (such as Gore-Tex and Zitex) have little or no effectiveness for retaining non-aqueous liquid electrolytes.

A few non-aqueous electrolyte systems have been attempted in electrochemical sensors with very limited success. For example, in a sensor disclosed in U.S. Pat. No. 4,184,937, a non-aqueous electrolyte comprising primarily propylene carbonate was employed with a Gore-Tex diffusion barrier membrane. Because of certain physiochemical characteristics of propylene carbonate, particularly surface tension, propylene carbonate was retained by the Gore-Tex membrane with limited success. Nonetheless, the electrolyte of that sensor could be made to flow through the diffusion barrier membrane with relative ease. Flow of electrolyte through the diffusion barrier membrane results in failure of an electrochemical sensor for two reasons: (1) bulk loss of electrolyte and (2) filling of the diffusion pores of the membrane with electrolyte, effectively ending its usefulness as an analyte-porous diffusion barrier. Other attempts at using non-aqueous electrolyte solutions, such as disclosed in U.S. Pat. No. 4,522,690, have involved gellation of the non-aqueous electrolyte to prevent loss thereof.

The present inventors have discovered that numerous and significant advantages can be achieved with the use of non-aqueous electrolyte systems. It is, thus, very desirable to develop electrochemical sensors in which non-aqueous electrolyte systems can be used.

SUMMARY OF THE INVENTION

Generally, the present invention provides an electrochemical sensor comprising at least two electrochemically active electrodes (typically a working electrode and a counter electrode), a non-aqueous electrolyte system and a diffusion barrier through which the analyte is mobile in its gas phase but through which the non-aqueous electrolyte system is substantially immobile. The diffusion barrier thus allows an analyte in its gas phase to enter the sensor, while substantially preventing the non-aqueous electrolyte from exiting the sensor. Preferably, the working electrode comprises an electrochemically active material on a porous membrane support. Similarly, the counter electrode preferably comprises an electrochemically active material on a porous membrane support.

It is extremely difficult to exclude water from an electrolyte system in the vast majority of environments in which such systems are used. As used herein, the phrase non-aqueous electrolyte system refers to an electrolyte system that comprises less than approximately 10% water (on the basis of weight). Preferably, the non-aqueous electrolyte comprises less than approximately 5% water. More preferably, the non-aqueous electrolyte comprises less than approximately 1% water. Preferably, the non-aqueous electrolyte systems of the present invention include an ionic charge carrying solute such as, for example, lithium perchlorate or tetraethylammonium perchlorate (TEAP).

The diffusion barriers of the present invention are referred to herein as "oleophobic diffusion barriers." As used herein, the phrase "oleophobic diffusion barrier" refers generally to a diffusion barrier through which the analyte is mobile in its gas phase but through which non-aqueous liquids are substantially immobile. Such oleophobic diffusion barriers are substantially resistant to bulk flow of low-surface tension liquids (such as the present non-aqueous electrolyte systems) therethrough at internal pressures generally experienced in electrochemical sensors. As used herein, the phrase "low-surface tension liquids" refers generally to liquids having a surface tension less than that of water. Preferably, the oleophobic diffusion barriers of the present invention are also hydrophobic (that is, they are also substantially resistant to the bulk flow of water therethrough at internal pressures generally experienced in electrochemical sensors). Diffusion barriers that are both hydrophobic and oleophobic are referred to as "multiphobic" herein. The diffusion barriers of the present invention are also preferably substantially chemically inert and thermally inert under the conditions in which electrochemical sensors of the present invention are typically used.

One method for measuring the oleophobicity of a diffusion barrier membrane is provided by Quality Assurance Test Method 713 of W. L. Gore & Associates, Inc. A summary of the procedures undertaken in Quality Assurance Test Method 713 is provided in the Appendix hereto. Under Quality Assurance Test Method 713, the present diffusion barriers preferably achieve a repellancy rating of at least 3. More preferably, the present diffusion barriers achieve a repellancy rating of at least 4. Other methods for determining the resistance to bulk flow of liquids or gases are provided, for example, by ASTM designations F 739-91 and F 1383-92.

Preferably, diffusion barriers for use in the present invention comprise films or membranes having a thickness in the range of approximately 1 to approximately 40 mils. More preferably, the thickness of such diffusion barrier membranes or films is in the range of approximately 3 to approximately 20 mils. Most preferably, the thickness of the diffusion barrier membranes or films is in the range of approximately 8 to approximately 12 mils. Preferably, these diffusion barriers have equivalent pore sizes in the range of approximately 0.03 to approximately 5 $\mu$m. As used herein, the terms "pore(s)" or porous preferably refer to materials having holes or channels therethrough of an equivalent pore size such that diffusion therethrough is essentially non-Knudsen diffusion.

By allowing the use of non-aqueous electrolytes, the present invention vastly expands the number of acceptable electrochemical sensor systems that may be employed to detect a wide range of analytes. Such analytes may exist in their gas phase or be dissolved in liquids. The electrochemistry of non-aqueous electrolytes is much broader and more varied than the electrochemistry of aqueous systems. Additionally, it has been discovered that the functionality of traditionally aqueous sensor systems (for example, electrochemical sensors for the detection of carbon monoxide (CO) and hydrogen sulfide ($H_2S$)) may be substantially improved by the use of non-aqueous electrolyte systems.

Unlike aqueous systems, non-aqueous electrolyte systems are substantially resistant to deleterious effects upon sensor performance resulting from widely varying humidity conditions. In that regard, unlike aqueous systems, non-aqueous electrolyte systems do not gain or lose substantial water to the surrounding environment. Thus, non-aqueous electrolyte systems can be used at extremes of relative humidity. It has also been discovered that for many analyte gases, non-aqueous electrolytes provide better sensor performance than aqueous electrolyte systems. In that regard, non-aqueous electrolyte systems tend to have lower zero gas currents and lower intrinsic noise levels than aqueous electrolyte systems, thereby improving the lower detection limits for particular analyte sensing electrochemistries. Further, by appropriate choice of the non-aqueous electrolyte system, different and/or broader sensor operating temperature ranges can be achieved than possible with aqueous electrolyte systems. Still further, changes in reaction kinetics can provide improved response times as compared to aqueous electrolyte systems.

DETAILED DESCRIPTION OF THE INVENTION

By appropriate choice of electrodes and electrolyte, the electrochemical sensors of the present invention can be fabricated to sense an extremely wide variety of analytes. For illustrative purposes, the present invention is discussed below in the context of a sensor for chlorine ($Cl_2$). The electrochemistry of such chlorine sensors is similar to the electrochemistry disclosed in U.S. Pat. No. 4,184,937.

Figure 1:
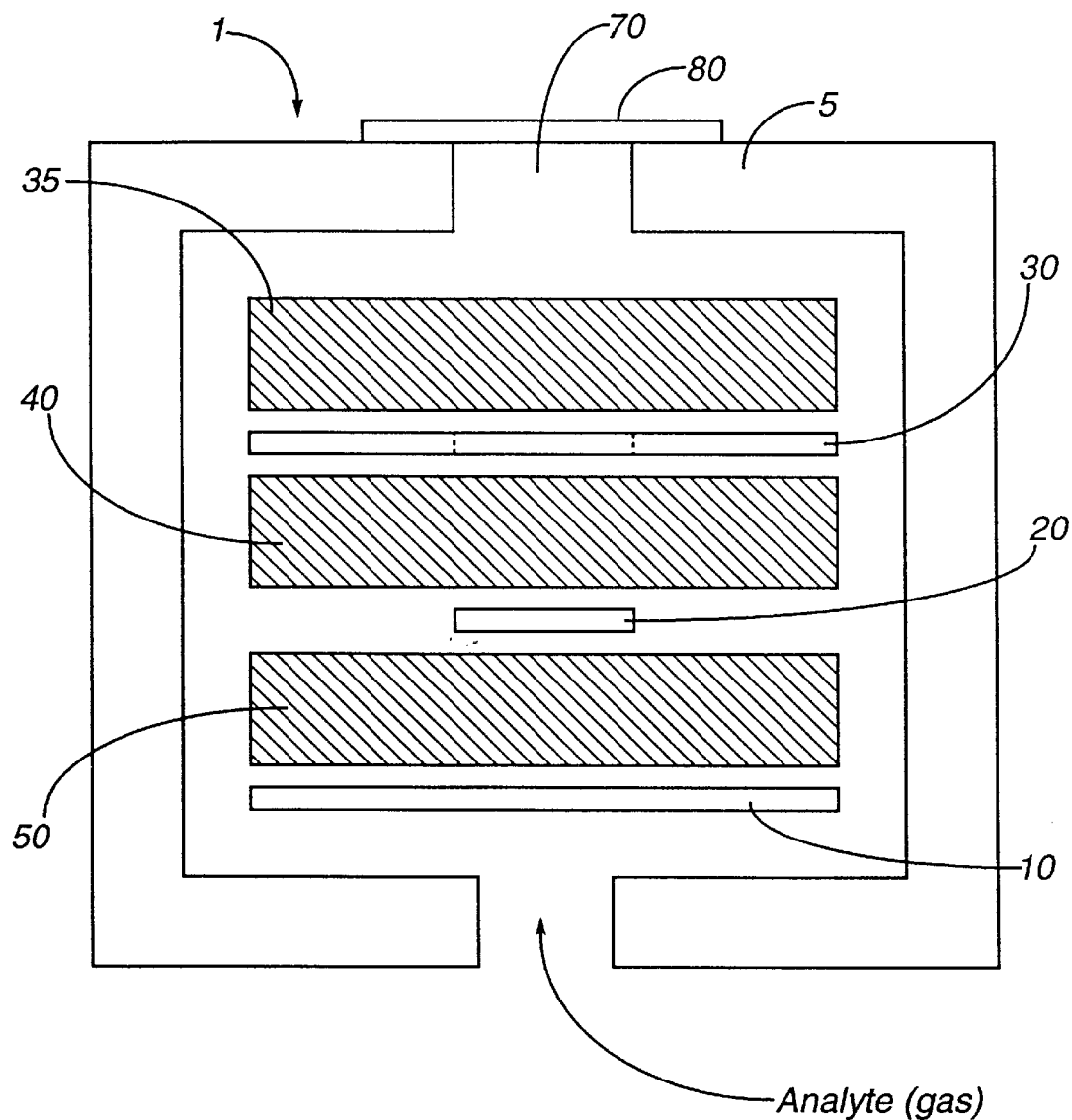
FIG. 1 illustrates schematically a cross-sectional view of an electrochemical sensor of the present invention.

As seen in FIG. 1, electrochemical sensor 1 preferably comprises a housing 5, enclosing a working electrode 10 and a counter electrode 30. Preferably, a reference electrode 20 is also provided to maintain working electrode 10 at a known potential. In fabricating electrochemical sensors 1 for use in the present studies, a porous spacer or wick 35 was first placed within housing 5. Counter electrode 30 was then placed into housing 5. A porous spacer or wick 40 was preferably then placed within housing 5 followed by reference electrode 20. A porous wick 50 was subsequently placed within housing 5 followed by working electrode 10. Wicks 40 and 50 in the present studies were fabricated from glass fiber matting.

After placement of working electrode 10 within housing 5, the perimeter of working electrode 10 was preferably sealed, for example, via heat sealing, to housing 5. In this embodiment, working electrode 10 itself acts as a diffusion barrier and thus preferably comprises an oleophobic or a multiphobic support. The interior of housing 5 was then filled with a non-aqueous electrolyte such as propylene carbonate via opening 70. Upon filling of the interior of housing 5 with electrolyte, opening 70 was sealed, for example, via heat sealing, using an oleophobic or a multiphobic diffusion barrier 80. An example of a multiphobic diffusion barrier suitable for use in the present invention is a Zintex® film. Zintex is a multiphobic porous perfluorocarbon available from W. L. Gore and Associates, Inc. Another example of a multiphobic porous membrane for use in the present invention is the Repel brand of breathable, multiphobic microporous membrane available from Gelman Sciences Technology Ltd. of Ann Arbor, Mich. The Repel brand multiphobic membrane comprises a microporous membrane with a non-woven polyester backing. Another example of a multiphobic porous membrane for use in the present invention is the Durapel™ membrane available from Millipore Corporation of Bedford, Mass. It has been discovered that these multiphobic porous membranes prevent bulk flow of the present non-aqueous electrolyte systems therethrough even in the presence of an ionic, charge-carrying solute.

In the present studies, housing 5 was also placed within an outer housing (not shown). A detailed discussion of a preferred assembly for electrochemical sensor 1 is set forth in U.S. Pat. No. 5,338,429, the disclosure of which is incorporated herein by reference.

Wicks 40 and 50 operate to prevent physical contact of the electrodes but allow the liquid electrolyte to contact the electrodes and thereby provide ionic conduction and thus an electrical connection between working electrode 10 and counter electrode 30.

In the case of a sensor for the detection of chlorine, the electrochemically active surface of working electrode 10 preferably comprises gold (Au). More preferably, the electrochemically active surface of working electrode 10 comprises gold and an electrically conductive carbon. Electrodes comprising gold and various electrically conductive carbons were fabricated in the present studies. As used in connection with the present invention, the phrase "electrically conductive carbon" refers generally to carbons with resistances in the range of approximately 0.2 k$\Omega$ to 180 k$\Omega$ as determined using methods described in U.S. patent application Ser. No. 08/426,271.

Working electrodes 10 for use in electrochemical sensors 1 for the present studies were preferably fabricated via silk screen deposition of an ink comprising gold powder. This ink was preferably deposited via silk screening upon a Zintex film. Such silk screening techniques are well known in the art for use with electrodes comprising Gore-Tex or Zitex films. Zintex films were found to provide a good support for an electrochemically active material and also to provide a good diffusion barrier, allowing analyte in its gas phase to diffuse into the electrochemical sensor while preventing escape of the non-aqueous electrolytes. In that regard, Zintex films were found to prevent seepage of a non-aqueous electrolyte comprising propylene carbonate for at least up to two years, whereas seepage of that electrolyte occurs in less than six months in the case of a Gore-Tex film.

The gold ink may also be deposited using hand painting techniques (as known in the art with Gore-Tex or Zitex films). Preferably, a film comprising gold and having a thickness in the range of approximately 1 to 10 mil is deposited. As discussed above, the electrochemically active surface of working electrode 10 can further comprise electrically conductive materials other that gold such as, for example, electrically conductive carbon, Pt, Ag, Ir or $RuO_2$.

In the case of a chlorine sensor, a preferred material for the electrochemically active surface of reference electrode 20 is platinum (Pt). In the case of platinum, reference electrodes 20 for use in electrochemical sensors 1 for the present studies were preferably fabricated via hand painting deposition of an ink comprising platinum powder. This ink was preferably deposited via hand painting upon a porous film as discussed above for working electrode 10. Preferably, a film of electrochemically active material having a thickness in the range of approximately 1 to 10 mil is deposited.

Platinum is also a preferred electrochemically active material for the electrochemically active surface of counter electrode 30 in the case of a chlorine sensor. Such electrodes are preferably fabricated as discussed above for reference electrode 20. As reference electrode 20 and counter electrode 30 do not act as diffusion barriers in the embodiment of FIG. 1, the supports therefore need not be multiphobic and may comprise, for example, Zintex, Gore-Tex or Zitex.

After deposition of the films of electrochemically active materials as described above, the films are preferably sintered to fix the electrochemically active material upon the substrate Zintex such as described in U.S. Pat. No. 4,790,925 (in connection with Gore-Tex), the disclosure of which is incorporated herein by reference.

Figure 2:
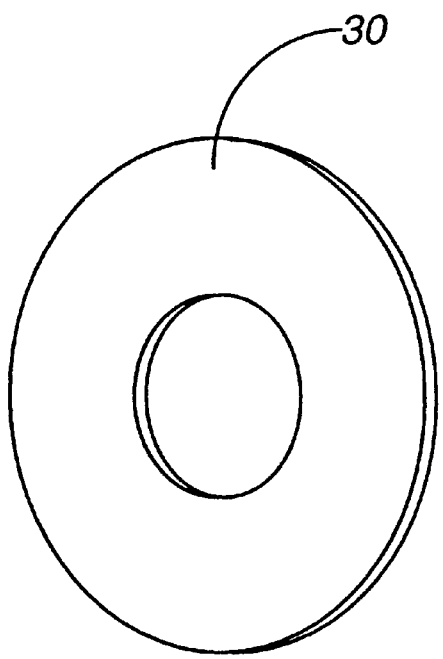
FIG. 2 illustrates a perspective view of an embodiment of the present counter electrode.
Figure 3:
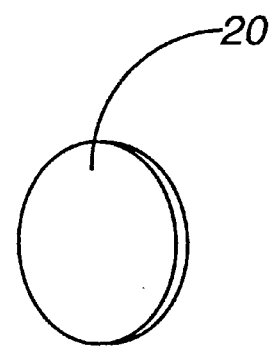
FIG. 3 illustrates a perspective view of an embodiment of the present reference electrode.

As illustrated in FIGS. 1 and 2, counter electrode 30 may be shaped in the general form of an annulus or ring. As illustrated in FIGS. 1 and 3, reference electrode 20 may be shaped in a generally circular form (that is, in the general shape of a disk). As clear to those skilled in the art, however, counter electrode 30, reference electrode 20 and working electrode 10 of electrochemical sensor 1 can be fabricated in many different shapes.

Preferably, electrochemical chlorine sensor 1 is subjected to a "cook-down" or "equilibration" period before use thereof to provide an adequately stable and low baseline. During the cook-down or equilibration period, electrochemical sensor 1 is stored at ambient conditions for a defined period of time. As common in the art, electrochemical sensor 1 is preferably maintained at a constant operating potential during the cook-down period. The operating potential of electrochemical sensor 1 is preferably in the range of approximately −0.2 V to +0.2 V versus the platinum/air electrode in electrolyte. More preferably, the operating potential of electrochemical sensor 1 is in the range of approximately −0.2 V to 0.0 V versus the platinum/air electrode in electrolyte.

Sensors 1 used in the present studies for the detection of chlorine included a working electrode of gold on Zintex, a reference electrode of platinum on Zintex or Gore-Tex and a counter electrode of platinum on Zintex or Gore-Tex. These sensors were subjected to a potential of approximately 0.0 V (versus the platinum/air electrode) during the cook-down period.

Preferably, a substantially stable baseline in the range of approximately −0.3 to 0.1 $\mu A$ is achieved during the cook-down period for an electrode having a geometric surface area of approximately 1 $cm^2$. It has been found that a cook-down period of approximately 24 hours is sufficient to provide an adequate baseline for electrochemical chlorine sensor 1. Electrochemical chlorine sensors 1 used in the studies discussed below were subjected to a minimum cook-down period of 24 hours. Preferably, a cook-down period of approximately 48 hours is allowed to ensure a stable baseline.

Figure 4:
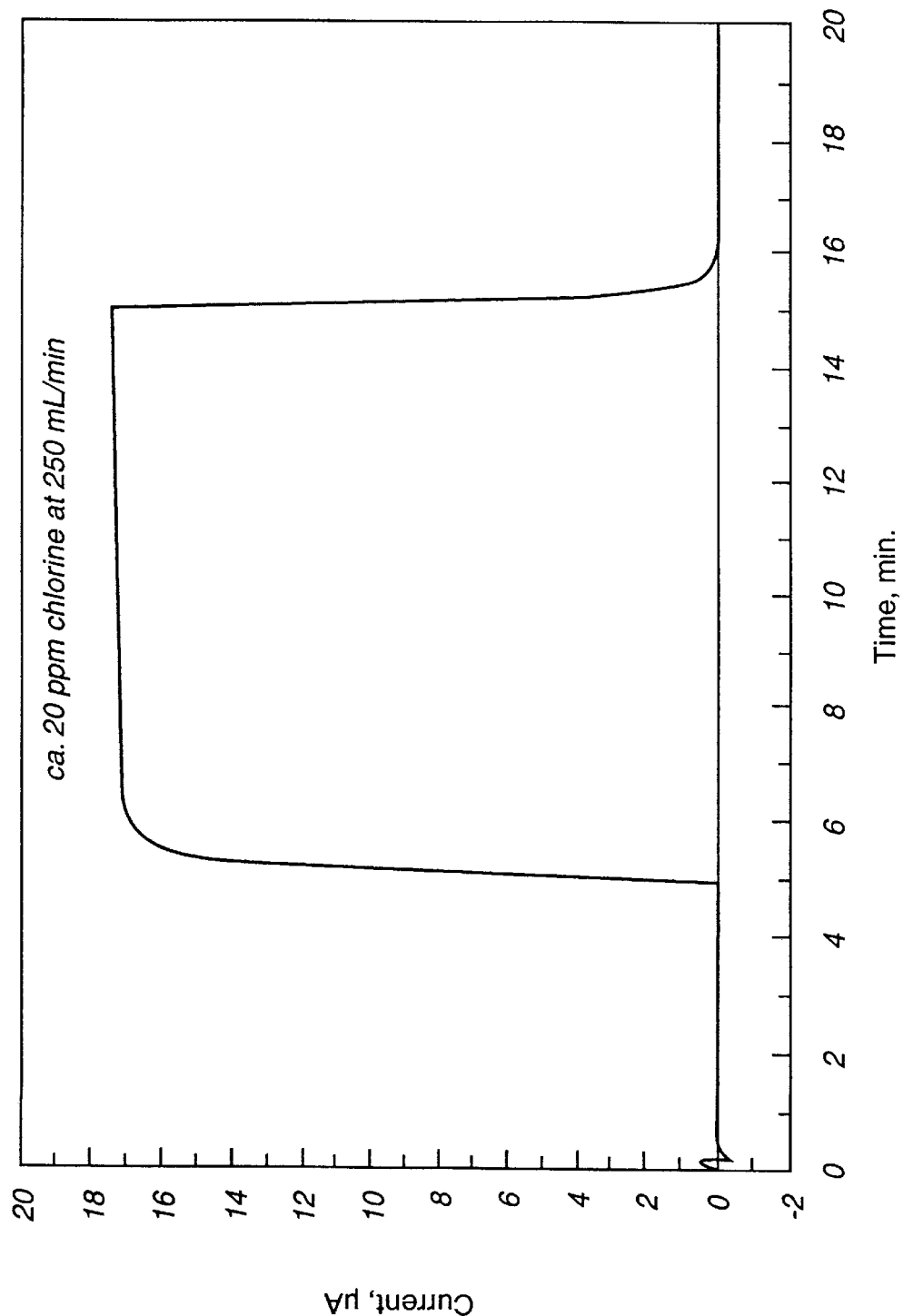
FIG. 4 illustrates a typical response of an electrochemical sensor under the present invention for the detection of chlorine.

Studies of sensors 1 were performed under computer control in which 20 sensors could be tested simultaneously. Generally, a baseline reading for each sensor was established as the sensor output after a ten-minute exposure to air (0 ppm chlorine). In testing for chlorine concentration, air was first applied to electrochemical sensors 1 for ten (10) minutes followed by application of air having a known concentration of chlorine (for example, 20 ppm chlorine) for 10 minutes. FIG. 4 illustrates a typical output (current, measured in $\mu A$) of electrochemical sensor 1 upon exposure to a 250 mL/min flow of air (0 ppm chlorine) for five (5) minutes, followed by exposure to a 250 mL/min flow of air comprising approximately 20 ppm chlorine for ten (10) minutes, followed by exposure to a 250 mL/min flow of air (0 ppm chlorine).

Response time and response time ratio (RTR) are empirical measures of the speed of response of a sensor and are critically dependent on the manner in which the test is performed (for example, the length of time the experiment lasts and/or the time at which the sensor reaches 100% of its final output). In the present studies, both response time and RTR were based upon a ten (10) minute exposure to test gas. RTR was calculated by dividing (i) the sensor output after one (1) minute of exposure to test gas by (ii) the sensor output after ten (10) minutes of exposure to chlorine test gas. Based upon a ten-minute test, RTR is also the percentage of final response (that is, response or output obtained after ten minutes) obtained in one minute. Response time was generally recorded as the 80% response time ($t_{80}$) or the 90% response time ($t_{90}$). The $t_{80}$ and the $t_{90}$ response times are the times, in seconds, required for the sensor to reach 80% and 90%, respectively, of the response or output obtained after ten minutes of exposure to test gas. The sensitivity (in units of $\mu A$/ppm chlorine) was established as the sensor output after ten (10) minutes of exposure to chlorine.

Some of the sensor cells studied had a pattern of five (5) inlet holes having an additive area approximately equal to the area of a single ⅜ inch diameter hole to allow the test gas to enter the sensor cells. An average output of approximately 0.8±0.2 $\mu A$/ppm was obtained under these experimental conditions. As clear to one of ordinary skill in the art, sensitivity can generally-be increased by increasing the total surface area of such inlet holes to allow more gas to enter the sensor cell.

The electrochemical sensors of the present studies were found to provide a substantially linear signal over at least the range of approximately 0 to 25 ppm chlorine. The response time of the present chlorine sensors was found to be less than approximately 60 seconds to 80% of final output for sensors of any age. The performance of the sensors was unaffected by changes in the humidity of the surrounding environment.

Interferrent studies undertaken with electrochemical sensors for the detection of chlorine under the present invention are summarized in Table 1. In Table 1, the data have been presented as the output that would be indicated for the application of 1.0 ppm of the test gas upon a properly calibrated sensor. As seen in Table 1, electrochemical sensors for the detection of chlorine under the present invention are substantially insensitive to chemical species other than chlorine.

TABLE 1

| Test Gas | ppm of Chlorine Indicated (based upon 1 ppm of test gas) |
|---|---|
| chlorine | 1.0 |
| ethylene | 0.0 |
| toluene | 0.0 |
| NO | 0.0 |
| $H_2S$ | −0.14 |
| $SO_2$ | 0.0 |
| $NO_2$ | 0.01 |
| CO | 0.0 |
| HCl | 0.01 |
| HCN | 0.01 |
| ethanol | 0.0 |
| hydrogen | 0.0 |
| methane | 0.0 |
| ammonia | −0.01 |

Sensors under the present invention were fabricated for the detection of analytes other than chlorine as well. For example, sensors comprising a multiphobic diffusion membrane (for example, Zintex) for the detection of hydrogen cyanide were fabricated. These sensors comprised a working electrode including an electrochemically active material comprising silver (Ag) on a Zintex membrane. The reference and counter electrodes comprised platinum on Zintex or Gore-Tex. The sensors also included an electrolyte comprising a mixture of propylene carbonate and triethanolamine (2,2',2"-nitrilotriethanol) with TEAP as an ionic component. The operating potential of the HCN sensor was preferably in the range of approximately −0.05 to 0.0 V versus the platinum/air electrode in the electrolyte. An average baseline of less than approximately −0.5 $\mu A$ and an average sensitivity of approximately 2.2 $\mu A$/ppm were obtained. An average response time, $t_{90}$, of less than 60 seconds was also achieved.

Likewise, sensors for the detection of saturated and unsaturated hydrocarbons were fabricated. For example, a sensor for the detection of methane was fabricated comprising a working electrode including platinum applied to a Zintex membrane. The sensor also comprised a reference electrode and counter electrode, each of which comprised platinum on Zintex or Gore-Tex. These sensors included a non-aqueous electrolyte system comprising γ-butyrolactone (dihydro-2 (3H)-furanone) with lithium perchlorate as an ionic charge carrier. The operating potential of the methane sensor was preferably in the range of approximately 0.0 to 0.50 V versus the platinum/air electrode in the electrolyte. An average baseline in the range of approximately 0.5 $\mu$A to 50 $\mu$A was experienced (depending upon the operating potential). An average sensitivity of approximately 0.1 $\mu$A/ppm and an average response time $t_{90}$ of less than 60 seconds were achieved.

Although the present invention has been described in detail in connection with the above examples, it is to be understood that such detail is solely for that purpose and that variations can be made by those skilled in the art without departing from the spirit of the invention except as it may be limited by the following claims.

APPENDIX

QUALITY ASSURANCE TEST METHOD 713

I. TITLE:
   OIL TEST, OIL REPELLENCY/OLEOPHOBICITY
II. PURPOSE:
   To measure the degree of oil repellency/oleophobicity of membrane or laminate. Oil repellency determines whether the member will continue to vent gasses while in contact with low surface tension liquids.
III. REFERENCES:
   1. AATCC 118–1989
   2. MSDS's of test liquids
IV. EQUIPMENT:
   1. Fume Hood
   2. Test Liquids 3 through 8
   3. Black Table Top
   4. Eye droppers or 5 ml transfer pipettes
V. SAMPLING PLAN:
   One specimen ~8" × full width from beginning and end of roll. Indicate "R" side.
VI. SAFETY PRECAUTIONS:
   1. Safety glasses and gloves should be worn by operator.
   2. Testing will be performed within a properly maintained laboratory fume hood.
   3. Refer to appropriate MSDS for proper handling of liquids.

| AATCC Oil Repellency Rating Number | Liquid Composition |
|---|---|
| 3 | n-hexadecane |
| 4 | n-tetradecane |
| 5 | n-dodecane |
| 6 | n-decane |
| 7 | n-octane |
| 8 | n-heptane |

VII. PROCEDURE:
   1. Place specimen flat on black surface with the membrane side up. If specimen curls up, edges should be taped down to the surface.
   2. Begin with test liquid member 3. Place a series of small drops (~3/16" in diameter) of test liquid across the width of the specimen. Begin at the yellow edge and continue across the specimen ~ every 3/4" to the red edge. For narrower samples, place at least 5 drops across the width.
   3. Observe sample for wetting and/or wicking in three zones across the specimen; yellow, center and red. The yellow zone extends from the yellow edge to a point 1/3 across the width of the sample. The center zone extends from red edge of yellow zone to a point 2/3 across the width of the sample. The red zone extends from red edge to a point 1/3 aross the web width. (See FIG. 5A.) Wetting of the membrane is evidenced by the normally white opaque surface becoming translucent to transparent and thereby appearing dark on a black table top. Wicking appears as wetting, however the darkening of the membrane occurs outside the drop area of the membrane.

APPENDIX-continued

QUALITY ASSURANCE TEST METHOD 713

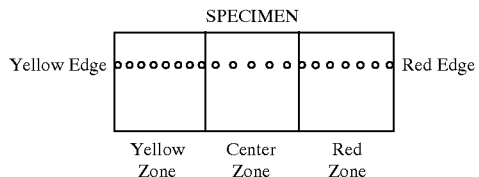

FIG. 5A

4. Observe the drops for 30 seconds from ~ a 45° angle at a distance of 12 inches.
   5. Repeat steps two through four with liquids in numerical order until wetting or wicking of the membrane occurs.
      a. When wetting or wicking occurs in any of the zones, record the liquid number of the previous nonwetting test liquid and the zone.
   6. Continue this procedure until all zones show obvious signs of wetting or wicking on the membrane by the test liquids within 30 seconds.
   7. The oil rating for each zone is the number of the last test liquid to not show obvious wetting after 30 seconds. The oil rating for the specimen is recorded as the oil rating for each zone.
      Example:

Specimen Oil Rating

| Yellow | Center | Red |
|---|---|---|
| 4 | 5 | 4 |

8. Test liquids applied on the specimens should be allowed to evaporate within the Fume Hood overnight. Tested specimens should be disposed of within an approved waste container.

What is claimed is:

1. An electrochemical sensor comprising a housing, the housing having disposed therein a working electrode, a counter electrode, a non-aqueous electrolyte system and an oleophobic diffusion barrier, the oleophobic diffusion barrier allowing an analyte in the analyte's gas phase to enter the housing while substantially preventing the non-aqueous electrolyte system from flowing therethrough, the non-aqueous electrolyte system comprising approximately 0 to approximately 10% water, the oleophobic diffusion barrier achieving an oil repellency rating of at least 3 under Quality Assurance Test Method 713.

2. The electrochemical sensor of claim 1 wherein the electrolyte system comprises a non-liquid ionic charge carrier.

3. The electrochemical sensor of claim 2 wherein the working electrode comprises an electrochemically active material supported upon a porous membrane.

4. The electrochemical sensor of claim 1 wherein the counter electrode comprises an electrochemically active material supported upon a porous membrane.

5. An electrochemical sensor comprising a housing, the housing having disposed therein a working electrode, a counter electrode, a non-aqueous electrolyte system and a multiphobic diffusion barrier, the multiphobic diffusion barrier allowing an analyte in the analyte's gas phase to enter the housing while substantially preventing the non-aqueous electrolyte system and water from flowing therethrough, the non-aqueous electrolyte system comprising approximately 0 to approximately 10% water, the multiphobic diffusion barrier achieving an oil repellency rating of at least 3 under Quality Assurance Test Method 713.

6. The electrochemical sensor of claim 5 wherein the electrolyte system comprises a non-liquid ionic charge carrier.

7. The electrochemical sensor of claim 5 wherein the working electrode comprises an electrochemically active material supported upon a porous membrane.

8. The electrochemical sensor of claim 5 wherein the counter electrode comprises an electrochemically active material supported upon a porous membrane.

9. An electrochemical sensor comprising a housing, the housing having disposed therein a working electrode including an electrochemically active surface comprising gold, a counter electrode including an electrochemically- active surface comprising platinum, a reference electrode including an electrochemically active surface comprising platinum, a non-aqueous liquid electrolyte system and an oleophobic diffusion barrier, the oleophobic diffusion barrier allowing an analyte in the analyte's gas phase to enter the housing while substantially preventing the non-aqueous liquid electrolyte system from flowing therethrough to exit the housing, the non-aqueous electrolyte system comprising approximately 0 to approximately 10% water, the oleophobic diffusion barrier achieving an oil repellency rating of at least 3 under Quality Assurance Test Method 713.

10. The electrochemical sensor of claim 9 wherein the oleophobic diffusion barrier also substantially prevents the passage of water therethrough.

11. The electrochemical sensor of claim 10 wherein the electrolyte system comprises propylene carbonate.

12. The electrochemical sensor of claim 10 wherein the electrolyte system further comprises lithium perchlorate.

\* \* \* \* \*